United States Patent [19]

Bauer et al.

[11] Patent Number: 5,133,756
[45] Date of Patent: Jul. 28, 1992

[54] PROCESS FOR PRODUCING A BONE REPLACEMENT MATERIAL

[75] Inventors: Gerd Bauer, Niederndorf; Freimut Vizethum, Schwetzingen, both of Fed. Rep. of Germany

[73] Assignee: Merck Patent Gesellschaft mit Beschraenkter Haftung, Darmstadt, Fed. Rep. of Germany

[21] Appl. No.: 458,710
[22] PCT Filed: Aug. 9, 1988
[86] PCT No.: PCT/EP88/00711
§ 371 Date: Feb. 20, 1990
§ 102(e) Date: Feb. 20, 1990
[87] PCT Pub. No.: WO89/01347
PCT Pub. Date: Feb. 23, 1989

[30] Foreign Application Priority Data

Aug. 19, 1987 [DE] Fed. Rep. of Germany ....... 3727606

[51] Int. Cl.$^5$ .......................... A61F 2/28; A61F 2/30; A61F 2/54
[52] U.S. Cl. ....................................... 623/16; 623/18; 623/66; 623/901
[58] Field of Search ................. 623/16, 66; 433/201.1

[56] References Cited

U.S. PATENT DOCUMENTS 4,314,380  2/1982  Miyata et al. ....................... 433/201

*Primary Examiner*—David Isabella
*Assistant Examiner*—Dinh X. Nguyen
*Attorney, Agent, or Firm*—Millen, White & Zelano

[57] ABSTRACT

According to a process for producing a bone replacement material, natural bones are used as raw material, the soft parts of the bones are removed, as well as any residual organic substances, and the remaining osseous substance is finally sintered at temperatures between 1100 degrees and 1500 degrees Celcius. In order to simplify such a process and to ensure a more gentle processing of the inorganic bone matrix, the bones are dried at an increased temperature, maximum 550 degrees Celcius, with a reduced air supply or in a reducing atmosphere, then the temperature of the bones is increased during the following step up to 750 degrees to 800 degrees Celcius, with an increased air supply, and finally the bones are sintered.

10 Claims, No Drawings

PROCESS FOR PRODUCING A BONE REPLACEMENT MATERIAL

The invention relates to a process for producing a bone replacement material in which natural bones are used as starting material, the soft tissues are removed from the bone, a removal of the residual organic substances is effected and the remaining osseous substance is then sintered at temperatures between 1100° and 1500° C.

It is known that it is possible and preferable to produce bone replacement material, which is penetrated by the tissue of the body and not rejected by this tissue, from natural bone material from which the organic substances have been removed, and the essentially unchanged matrix of which is then sintered (U.S. Pat. No. 4 314 380; EP-A 141004). In these known processes, after the mechanical removal of soft tissues, a considerable portion of the organic material is extracted from the bone material by treating the bone with a solution of hydrogen peroxide. Apart from such a treatment being troublesome and requiring precautions because of the bleaching effect of a solution of this type, the removal of the organic material from the bone matrix is not entirely successful in this way. During the subsequent incineration of the bone at elevated temperatures the remaining organic material is combusted, and volatile components can arise in such amounts that the microstructure of the bone matrix is damaged by this. It has to be taken into account here that the bone matrix gains its mechanical strength only on sintering, and before sintering the matrix shows only very poor mechanical stability.

The object of the invention is to improve a process of the abovementioned type in such a way that, while simplifying the production process, a milder treatment of the bone material and a higher degree of retention of the structure of the bone material is made possible.

In a process of the kind described in the introduction this object is achieved according to the invention by drying the bone at an elevated temperature of up to a maximum of 150° C. after the removal of the soft tissues, then raising the temperature with a reduced air supply or in a reducing atmosphere to about 550° C., in a following step heating the bone to a temperature of between 750° and 800° C. with an increased air supply, and by subsequent sintering.

Owing to the fact that the bone material, after drying under mild conditions at a maximum of 150° C., is subjected to an elevated temperature with a reduced air supply or in a reducing atmosphere, pyrolysis takes place, that is to say a thermal decomposition of the organic material, which leads to a carbonization of the organic bone material with elimination of volatile constituents.

In the next step the carbon is then combusted with an increased air supply at temperatures of up to a maximum of 800° C. Volatile constituents are no longer present during this pure combustion process, so that damage to the inorganic bone matrix is avoided.

The described process has the advantage that no chemical treatment of the bone whatsoever is necessary, on the contrary after the mechanical removal of the soft tissues the bone is subjected only to heat treatment which is divided up into various sections.

It can be provided that the bone is dried at an elevated temperature of up to a maximum 150° C. for between 24 and 72 hours in order that the drying is carried out under conditions which are as mild as possible. Moreover it is beneficial if, during drying, the temperature is gradually increased from the ambient temperature to the maximum temperature of 150° C. Gradually means here that the increase can take place continuously throughout the whole period of drying. This avoids the onset of an explosive vaporization at the boiling point of water, which could damage the bone material. Gradually increasing the temperature results in continuous vaporization of the volatile constituents throughout the whole period of drying, with no major evolution of gas occurring.

It can also be provided that the bone is treated for approximately 8 to 24 hours with a reduced air supply or in a reducing atmosphere. During this step the temperature is preferably increased gradually to 550° C., once again gradually meaning that the temperature is steadily increased throughout the whole period of treatment. This measure also contributes to the sequential formation of gaseous constituents of different volatilities so that at no point does undesirably great evolution of gas occur.

The incineration of the bone with an increased air supply and at a temperature of 750° to 800° C. is preferably carried out for 4 to 24 hours, it also possibly being beneficial here to increase the temperature gradually to approximately 800° C. when incinerating the bone.

The sintering is preferably carried out for 2 to 20 hours at maximum temperatures of 1100 to 1400° C., and the cooling takes place slowly, for example over a period of 10 to 20 hours. It has been found that it is especially advantageous if, after sintering, the bone is, during cooling, kept at a temperature of between 1120° and 1160° C. for a period of 2 to 6 hours and the bone material then cools according to the characteristic of the oven. An increase in mechanical strength is obtained by this because small amounts of secondary phase can be induced to crystallize and recrystallize.

Some examples of carrying out the process according to the invention are given below:

EXAMPLE 1

Animal bone is boiled for partial removal of its organic components. Adhering soft tissues are removed mechanically.

The desired shape is obtained for example by a reduction in size using a saw.

Drying with a continuous increase in temperature from room temperature to 150° C. in the course of 26 h (hour) then follows.

A pyrolysis of the organic components by an increase in temperature for example at 25 K/h (Kelvin/hour) with a reduced air supply follows.

The material is then heated to 800° C. with an increased air supply for example at 25 K/h. The subsequent sintering process is carried out from room temperature to for example 1450° C. with a rate of heating of 100 K/h and a maintenance time of 10 hours. The cooling takes place likewise at a rate of 100 K/h.

EXAMPLE 2

The preparation and pyrolysis steps with the subsequent burning out are as in example 1, the sintering takes place with a rate of heating of 100 K/h to 1250° and a maintenance time of 15 hours. During the process of cooling according to the characteristics of the oven a maintenance time of 4 hours at 1120° is inserted.

It has been found that the mineral phase of the bone is retained completely when the maximum temperature of sintering is at 1400° C. or below. With higher maximum temperatures of sintering a thermal decomposition of the mineral phase starts and leads to an increase in absorption in the body. In this way it is possible to change specifically the composition of the bone ceramic to induce faster or slower absorption. This is desirable for some applications, for example in the therapy of osteomyelitis.

We claim:

1. In a process for producing a bone replacement material in which natural bones are used as starting material, soft tissues are removed from the bone, a removal of residual substances is effected and remaining osseous substance is then sintered at temperatures between 1100° and 1500° C., the improvement wherein:

the bone is dried at an elevated temperature of up to a maximum of 150° C. after removal of the soft tissues;

the temperature is then raised to about 550° C. wherein pyrolysis occurs with a reduced air supply or in a reducing atmosphere; and in a following step the bone is heated to a temperature of between 750° and 800° C. with an increased air supply, and in that sintering takes place subsequently.

2. A process according to claim 1, wherein the bone is dried at an elevated temperature of up to a maximum of 150° C. for between 24 and 72 hours.

3. A process according to claim 1 wherein, during drying, the temperature is gradually increased from ambient temperature to the maximum temperature of 150° C.

4. A process according to claim 1, wherein the bone is treated for approximately 8 to 24 hours during the step with a reduced air supply or in a reducing atmosphere.

5. A process according to claim 1 wherein the temperature is gradually increased to 550° C. during the treatment of the bone with a reduced air supply or in a reducing atmosphere.

6. A process according to claim 1, wherein the bone is kept at a maximum temperature of 760° to 800° C. for approximately 4 to 24 hours during the step with an increased air supply.

7. A process according to claim 1 wherein the temperature is gradually increased to approximately 800° C. when incinerating the bone with an increased air supply.

8. A process according to claim 1, wherein the sintering is carried out for 2 to 20 hours at maximum temperatures of 1100° to 1400° C.

9. A process according to claim 1, wherein the temperature during sintering is gradually increased to the maximum temperature of sintering.

10. A process according to claim 1, wherein, after sintering, the bone is, during cooling, kept at a temperature of between 1120° to 1160° C. for a period of 2 to 6 hours.

* * * * *